(12) United States Patent
Delrieu et al.

(10) Patent No.: US 8,025,892 B2
(45) Date of Patent: *Sep. 27, 2011

(54) COSMETIC PARTICULATE GEL CARRIERS FOR TOPICALLY APPLIED ACTIVE AGENTS

(75) Inventors: Pascal E. Delrieu, Castanet Tolosan (FR); Li Ding, Castanet Tolosan (FR)

(73) Assignee: Kobo Products, Inc., South Plainfield, NJ (US)

( * ) Notice: Subject to any disclaimer, the term of this patent is extended or adjusted under 35 U.S.C. 154(b) by 1620 days.

This patent is subject to a terminal disclaimer.

(21) Appl. No.: 10/017,259

(22) Filed: Nov. 12, 2001

(65) Prior Publication Data

US 2002/0086042 A1 Jul. 4, 2002

Related U.S. Application Data

(63) Continuation of application No. 09/431,742, filed on Nov. 1, 1999, now Pat. No. 6,319,507, which is a continuation-in-part of application No. PCT/IB98/00977, filed on May 1, 1998.

(51) Int. Cl.
*A61K 31/14* (2006.01)
*A61K 8/02* (2006.01)
*A61K 9/14* (2006.01)
*A61K 9/50* (2006.01)
*C11D 1/62* (2006.01)

(52) U.S. Cl. ............ 424/401; 424/70.28; 424/484; 424/485; 424/486; 424/499; 424/500; 424/501; 514/642

(58) Field of Classification Search .......... 424/70.28, 424/489, 493, 401, 484, 485, 486, 499, 500, 424/501; 264/14, 5; 514/642, 952

See application file for complete search history.

(56) References Cited

U.S. PATENT DOCUMENTS

| | | | |
|---|---|---|---|
| 4,465,693 A | 8/1984 | Strauss et al. | |
| 4,834,734 A * | 5/1989 | Morganti | 604/368 |
| 4,847,076 A | 7/1989 | Deshpande et al. | |
| 4,970,067 A | 11/1990 | Panandiker et al. | |
| 4,994,273 A | 2/1991 | Zentner et al. | |
| 5,077,211 A | 12/1991 | Yarosh | |
| 5,135,748 A | 8/1992 | Ziegler et al. | |
| 5,151,264 A | 9/1992 | Samain et al. | |
| 5,169,624 A | 12/1992 | Ziegler et al. | |
| 5,171,526 A | 12/1992 | Wong et al. | |
| 5,183,493 A * | 2/1993 | Brandau et al. | 75/335 |
| 5,288,484 A | 2/1994 | Tashjian | |
| 5,302,389 A | 4/1994 | Kripke et al. | |
| 5,314,915 A | 5/1994 | Rencher | |
| 5,352,458 A | 10/1994 | Yarosh | |
| 5,417,982 A | 5/1995 | Modi | |
| 5,449,519 A | 9/1995 | Wolf et al. | |
| 5,457,093 A | 10/1995 | Cini et al. | |
| 5,494,533 A | 2/1996 | Woodin, Jr. et al. | |
| 5,496,852 A | 3/1996 | Oliver | |
| 5,534,247 A | 7/1996 | Franjac et al. | |
| 5,961,990 A | 10/1999 | Delrieu et al. | |
| 5,968,794 A | 10/1999 | Samain et al. | |
| 6,096,834 A * | 8/2000 | Tremont | 525/355 |
| 6,300,468 B1 * | 10/2001 | Bretz et al. | 528/497 |
| 6,319,507 B1 | 11/2001 | Delrieu et al. | |

FOREIGN PATENT DOCUMENTS

| | | |
|---|---|---|
| EP | 0 470 872 A1 | 2/1992 |
| WO | WO 96/29080 | 9/1996 |
| WO | WO 9804618 A1 * | 2/1998 |

OTHER PUBLICATIONS

Sperling, Introductin to Physical Polymer Science, 2001, pp. 63-68.*
Grulke, Polymer Handbook, 199, pp. 519-524, 526-533, 544-550 and 557-559.*
Hsiu et al., Biochemistry, 1964, 3(1), 61-66.*
Crodacel Q Range, Product Sheet, Croda Chemicals Ltd., Jul. 1989.
E. Desmond Goddard and James V. Gruber, Principles of Polymer Science and Technology in Cosmetics and Personal Care, 1999, 339, 331-335, 346-349, 353-356, 361-376, 391, 412-419, 446-448, vol. 22, Marcel Dekker, Inc. New York.

* cited by examiner

*Primary Examiner* — Johann Richter
*Assistant Examiner* — Abigail Fisher
(74) *Attorney, Agent, or Firm* — Handal & Morofsky LLC

(57) ABSTRACT

Gel particles or beads can be prepared by forming a hot aqueous solution of a gelling agent, and discharging the hot gelling agent solution through a discharge orifice into a cold moving stream of hydrophobic liquid so that the gelling agent solution cools rapidly and good quality gel particles coalesce in the cold hydrophobic liquid stream. The cold hydrophobic liquid stream can be contained in a conduit so that the cold hydrophobic liquid stream moves past the discharge orifice and exerts a force on hot solution in the discharge orifice, the force acting to withdraw the hot solution from the discharge orifice. Optionally, the gel particles can be crushable gel beads 10 formed of an agar complex providing cosmetic, pharmaceutical, etc. delivery vehicles for topical delivery of biologically or cosmetically active agents. Preferred agar beads 10 are complexes of a continuous phase of agar gel 12 in a self-supporting solid or semi-solid form with a restraining polymer 14. Various active agents 16 may be bound to restraining polymer 14, for, example ascorbic acid, lactic acid or papain.

29 Claims, 5 Drawing Sheets

COSMETIC PARTICULATE GEL CARRIERS FOR TOPICALLY APPLIED ACTIVE AGENTS

CROSS-REFERENCE TO RELATED APPLICATIONS

This application is a continuation of our U.S. patent application Ser. No. 09/431,742 filed Nov. 1, 1999, now U.S. Pat. No. 6,319,507. application Ser. No. 09/431,742 was a continuation-in-part of our international patent application PCT/IB98/00977 filed 1 May 1998 which application claimed priority from our U.S. patent application Ser. No. 08/850,167 filed May 2, 1997 now U.S. Pat. No. 5,961,990. The disclosures of the aforementioned United States patents and patent applications and of the aforementioned international application, are hereby incorporated herein by reference thereto. The benefit of continuation status is not being claimed at this time with regard to applications numbers PCT/IB98/00977 and 08/850,167. However, this statement is made without prejudice to applicant's right to claim continuation status, with respect to another application, at any time during the pendency of the present application.

BACKGROUND OF THE INVENTION

1. Field of the Invention

This invention relates to a novel cosmetic or dermatological delivery system having a variety of applications for delivery of topically applied active agents to the skin, to methods of preparing such delivery systems and to cosmetic or dermatological formulations in which the delivery systems may be incorporated. Of particular interest are multiphase cosmetic formulations such as gels, creams and lotions.

One difficulty with known cosmetic delivery systems is that of protecting labile compounds from reacting prematurely. Furthermore, certain biologically active substances, e.g. alpha hydroxy acids, are known to benefit the skin by improving skin softness and appearance. However, many such actives tend to cause irritation because they have the capacity, if the local concentration is too high, to penetrate deeply through the stratum corneum to more sensitive living tissue. Accordingly, there is a need for a delivery system that can separate active agents from a formulating excipient or adjuvant and provide controlled release of the active substances at the point of application. It would also be advantageous to provide a delivery system for actives that permits localized concentration of actives at the point of delivery, for instance, at the skin's surface.

One approach is for actives to be bound to carrier molecules to provide a complex which will remain stable in cosmetic preparations. When the complex is applied to the skin, the active is released or dissociated from the delivery system and is absorbed into the skin to provide the desired effect. Such systems are known to the art, but they fail adequately to separate the actives from formulation ingredients. Nor do they provide a means for concentrating delivery of actives at a desired location, for example the skin's surface. Another problem encountered in delivering actives to the skin is that they may react undesirably with the delivery system itself. Cosmetic actives can be stabilized in suspensions and formulas as cosmetic preparations. However, formulating the thus stabilized actives requires elevated temperatures and varying pH levels which may modify the active and cause stability problems with the formulation.

Polyphenols such as procyanidin oligomers, are good examples of labile actives that are known to polymerize undesirably in reaction with common components of many cosmetic formulations. Polyphenols include catechins which are botanically derived antioxidant polyphenols extracted from grape seed, green tea and other woody plants. Catechins are useful for free radical scavenging in anti-ageing formulations to protect against the effects of ultraviolet light.

A multilayer particulate delivery systems for these and other active ingredients, and for controlled systemic release of drugs, is taught by Samain et al. in the U.S. Pat. No. 5,151,264. Samain et al. disclose what they describe as "biomimetic" carriers comprising an absorbent, solid, core of modified starch and an outer phospholipid coating which mimics a typical cellular membrane to avoid triggering the body's defenses to the incursion of foreign particles. Though Samain et al.'s multi-layer particles are very effective for many applications, it would be desirable to have a delivery system that provides additional options for release of the active at the delivery point or zone, and which permits quicker release at the skin's surface than is possible from Samain's dimensionally stable solid core particles.

Delivery systems for active substances having biologic or cosmetic activity, "actives" herein, can be either sustained release or controlled release systems. Sustained release systems release the active continuously from the moment of formulation. The active to be delivered is embedded within a matrix whose diffusion coefficient is low (lower than water for instance) so that the active slowly releases out of the matrix. This type of continuous release system is not suitable for cosmetic formulations because constant release of the active upon formulation of the system, for example into a cosmetic cream, creates instability affecting shelf life and effectiveness. In contrast, controlled release systems release the active when initiated by a particular event. The active is chemically or physically bound to a matrix in the controlled release system and is subsequently released when that bond is destroyed by an external event. For example, with the Samain et al. multilayer particles, the active ingredient is linked to the particle by means of ionic bonding. The release of the active is initiated by encounter with skin moisture, which has a relatively low ionic strength.

Gel forming polymers provide a delivery system by forming a matrix in which active substances can be entrapped. An example of a gel forming polymer is agar, also known as "agar-agar", a polysaccharide commonly used as a medium for electrophoresis and chromatography. It is known that agar can be formed into beads of various sizes for delivery of actives such as pharmaceutical drugs or even biological cells. A problem with agar beads is that they form a sustained release system which, as described above, is not suitable for cosmetic applications because release of the actives commences at formulation.

2. Description of Related Art Including Information Disclosed under 37 CFR 1.97 and 37 CFR 1.98

Cini et al U.S. Pat. No. 5,457,093 discloses a sustained release gel formulation for delivering growth factors to wound sites, especially ophthalmic wounds. Various polysaccharide gels are used, including agar. Cini's gels are not intended for formulation into cosmetics and would presumably dissolve or disperse and fail to protect their actives, if subjected to mixing with an aqueous phase cosmetic vehicle. The actives are continuously released from the gel from the moment the gel is incorporated into a cosmetic formulation containing an aqueous phase. Accordingly, Cini's gel formulations cannot be used in cosmetic emulsions that are required to have significant shelf lives.

Modi U.S. Pat. No. 5,417,982 discloses a controlled release delivery system where a polymer-gel matrix comprised of two-water-soluble polymers is incorporated into microspheres. Biodegradation of the microsphere matrix provides a controlled release oral or injection delivery system for administering therapeutic doses of proteins or polypeptides internally or systemically. Modi's system is apparently not intended for, and would not be suitable for, topical delivery and release of actives.

Rencher U.S. Pat. No. 5,314,915 provides a local anesthetic delivery system comprising a polymer blend of sodium carboxymethyl cellulose and xanthan gum or sodium alginate. Rencher's formulation is a continuous phase adhesive or teething gel, rather than being particulate, and does not provide a delivery system that will facilitate the incorporation of actives in a cosmetic or pharmaceutical formulation with good separation of the active from the formulation. Rencher's continuous phase system does not protect any adsorbed actives if incorporated into a cosmetic cream or lotion containing an aqueous phase.

Yarosh U.S. Pat. No. 5,077,211 discloses delivery of DNA repair enzymes in active form to living mammalian cells in situ by incorporating purified enzymes into liposomes which are diluted into media and added to target cells. The DNA enzymes are reportedly active topically and elsewhere to correct cellular deficiencies, stimulating generation of healthy tissue to replace aged or damaged skin. Yarosh's liposomes are prepared by rehydrating lipid mixture films with a concentrated, buffered, aqueous solution of the enzyme, agitating, sonicating and separating out the desired liposome spheres. Lipid mixtures used are based upon phosphatidyl choline (lecithin) as a primary ingredient, with dicetyl phosphate or stearylamine as secondary ingredients and with cholesterol an optional tertiary ingredient, see Examples 3 and 4.

According to Yarosh, the liposomes are incorporated into polyglycol gels, apparently at room temperature, for topical application, apparently under laboratory conditions. Consideration of Yarosh's delivery vehicles suggests that while they may be adequate for laboratory testing, they would not be suitable for commercial applications.

Yarosh U.S. Pat. No. 5,352,458 and Kripke et al. U.S. Pat. No. 5,302,389 disclose the use of Yarosh's DNA repair enzymes, prepared according to Yarosh '211, respectively for enhancing tanning by stimulating enhanced melanin production, and for suppressing UV-induced T-cell immune response and thence the associated redness, tenderness and inflammation.

Clearly, significant benefits might be obtained from a cosmetic or pharmaceutical formulation having a carrier to deliver such DNA repair, or other enzymes, in active form, for topical application to the skin by consumers with or without professional supervision. The difficulty is that enzymes are labile and subject to denaturing by formulation temperatures or pH conditions, or by reaction with cosmetic vehicles during the extended periods of shelf storage that are normal in the cosmetic and pharmaceuticals manufacturing and distribution chains.

Neither the liposomes described by Yarosh, nor the liposome gel would appear to offer sufficient protection to permit Yarosh or other enzymes to be formulated into consumer cosmetic products, such as creams, lotions or gels having adequate stability. The elevated processing temperatures, dispersing agents and extended shelf life required may decompose or denature not only the enzymes but their liposome carriers leading to unacceptable separation, loss of activity and the like.

There is accordingly a need for an esthetic cosmetic carrier for topically applied active agents that can protect labile actives such as botanical extracts, desquamating enzymes and the like, and deliver such agents to the skin in active form, while being suitable for formulation into traditional cosmetic vehicles. There are further needs for cosmetic or pharmaceutical delivery systems which offer separation of active from formulation ingredients and which can maintain that separation through typical formulation processes, especially those required for providing emulsions and for delivery systems which provide controlled release of actives at a delivery point and preferably also permit localized concentration of actives at the delivery point.

SUMMARY OF THE INVENTION

The invention, as claimed, is intended to provide a remedy for the problem of providing a delivery system for delivering labile and other actives to the skin, or other body surface, for topical application in a cosmetic or pharmaceutical formulation. It furthermore solves problems of delivering actives that may react undesirably with the delivery system itself, damaging the active or causing stability problems with the formulation.

Accordingly, the invention provides a protective cosmetic particulate gel delivery system for a topically applied active agent comprising discrete gel particles formed of:
  a) an agar gel; and
  b) a restraining polymer dispersed in the agar gel, the restraining polymer having sufficient molecular weight to prevent egress of the restraining polymer from the agar gel, having retention groups to bind the active agent to the restraining polymer for retention in the gel particles and being present in a proportion sufficient to deliver an effective amount of the active agent;
wherein the gel particles are manually crushable on the skin to increase the surface area of the gel particle material and expose the restraining polymer to the skin or other body surface for release of the active agent.

Preferably, active agent molecules are bound to the restraining polymer retention groups and the restraining polymer has an average molecular weight of at least 100,000 daltons. In a preferred embodiment, the active agent and the retention groups both comprise polar groups and are of opposite polarity whereby the active agent can bind ionically with the retention groups. A suitable restraining polymer is water-soluble and has a polysaccharide backbone substituted with strongly cationic quaternary ammonium groups which can act as retention groups for a range of active agents. The cationic ammonium groups are able to form stable ionic bonds with anionic actives which bonds can be broken to release the active upon topical application of the containing cosmetic composition.

Some suitable ionically bondable active agents are antioxidants, e.g. vitamin C (ascorbic acid), botanically derived polyphenols, procyanidin oligomers, free radical scavengers, and topically active enzymes. Desired nonionic actives, for example vitamin E (alpha-tocopherol), can bind to lipid groups on preferred restraining polymers, by hydrophobic interaction. While agar is a particularly preferred gel-forming agent, other gel-forming agents that meet the requirements of the invention can be used.

The invention thus provides a delivery system for delivering actives to the skin wherein one or more active agents is entrapped within a complexed-agar bead containing, in addition to agar, a restraining polymer to which the active bonds and from which it is not released until it reaches a target environment. The agar complex beads can be formed in various sizes to deliver actives, including pharmaceutical drugs or even biological cells, to the skin and applied to the skin as soft crushable beads.

Many desired active materials entrapped in an agar gel, leach out over time, especially if stored in an aqueous vehicle. In contrast, the restraining polymer has a molecular weight sufficient, for example 100,000 daltons or more, to prevent it from being released out of the agar matrix, so that, being bound to the polymer, the active is not released from the agar bead. The agar beads formed are preferably soft enough to be crushed on the skin during normal application of a cosmetic formulation.

The invention also provides a method of preparing agar gel particles comprising the steps of:
 a) dissolving agar in water heated to an elevated temperature sufficient to dissolve the agar, in a proportion of agar to water effective to form a gel at lower temperatures; and
 b) mechanically dispersing the agar solution in a cold hydrophobic liquid immiscible with the agar solution maintained at a temperature below the agar gelling point;
with the improvement that a water-soluble restraining polymer is included in the agar solution whereby the drops are formed into gel beads incorporating the restraining polymer.

Preferably, though not necessarily, the hot agar solution is cooled to an intermediate temperature above the gelling point of the agar solution prior to performing step b). In a preferred embodiment, which is simple and economic to practice, the agar-restraining polymer solution is mechanically dispersed in the cold hydrophobic liquid by using a rotating agitator. Using this method, the gel bead size can be controlled by selecting the rotation speed of the agitator.

In an alternative embodiment, the agar-restraining polymer solution is mechanically dispersed in the cold hydrophobic liquid by injection through a hollow needle to form drops, the needle having an internal dimension selected to provide a desired gel bead size.

An advantage of employing a cooling step is that temperature-sensitive active agents can be admixed with the cooled agar-restraining polymer solution, prior to step b), avoiding the higher temperatures required for step a). Other active agents can be admixed in step a). Either way, the active agent is effectively incorporated in the gel beads, where it will be protected from possibly damaging cosmetic, or pharmaceutical or other ingredients with which the beads may be formulated, and is available to be topically delivered by crushing the beads on the skin.

While reference is made herein to the skin as a delivery target for active agents, it will be appreciated that the nails, hair, mouth, teeth wound tissue, or other accessible endogenous body surfaces can be similarly targeted, depending upon the active and the cosmetic or medicament vehicle into which the beads are formulated.

BRIEF DESCRIPTION OF THE DRAWINGS

Some illustrative embodiments of the invention, and the best mode contemplated of carrying out the invention, are described in detail below with reference to the accompanying drawings in which:—

DETAILED DESCRIPTION OF THE PREFERRED EMBODIMENTS

All parts and proportions referenced in this description, unless otherwise stated, are on a weight or weight-for-weight basis.

Figure 1:
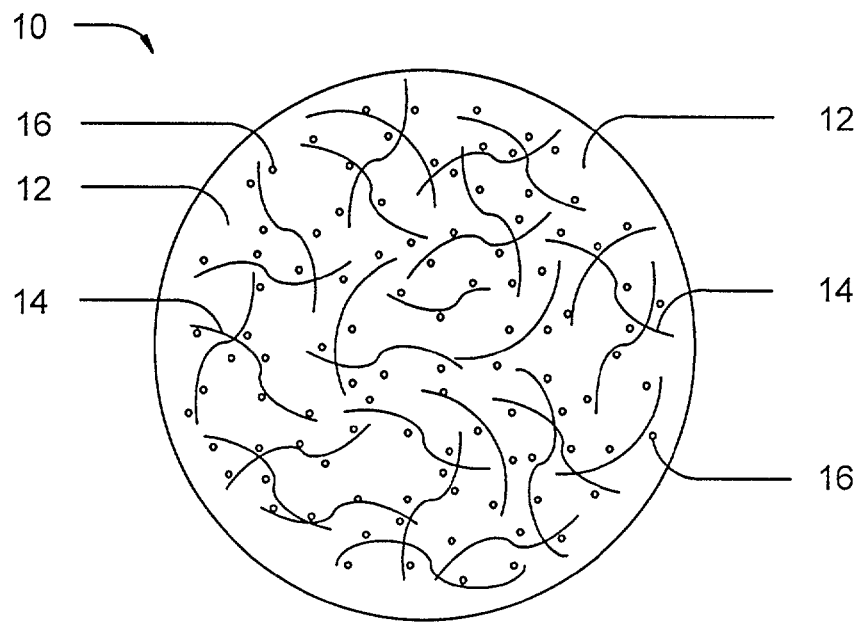
FIG. 1 is a schematic view of an embodiment of cosmetic gel particle carrier according to the invention which takes the form of an agar bead.
Figure 2:
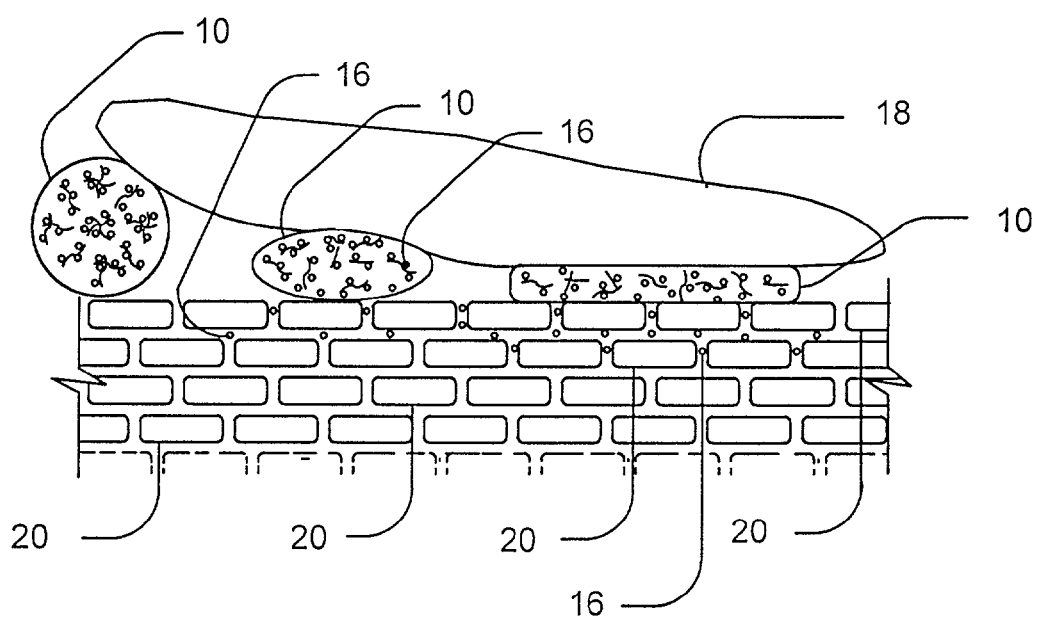
FIG. 2 is a schematic view showing several of the agar beads shown in FIG. 1 being crushed on the skin of a user.

Referring to FIGS. 1 and 2, a particularly preferred embodiment of particulate cosmetic gel carrier comprises relatively small agar particles or agar beads 10 having an average particle size measured in millimeters. The particles are small enough for cosmetic use, and preferably do not exceed 10 mm. in diameter, on average, but not so small as to penetrate the skin or skin pores. A minimum diameter, on average, is about 0.05 mm. (50 microns). A preferred range of particle sizes is from about 0.1 to 3.0 mm. in diameter, on average, with a more preferred range being from about 0.25 mm. to about 1 mm. in diameter, on average.

Preferred methods of producing the particles yield a well-focused size distribution, so that it is preferred that at least 80 percent of the particles, more preferably 90 percent of the particles, lie within a desired average particle size bracket extending up to about 30 percent either side of a targeted average. If desired, for particular applications, a more uniform product can be obtained by mesh filtration.

Agar beads 10 are complexes of a continuous phase of agar gel 12 in a self-supporting solid or semi-solid form with a restraining polymer 14. Dispersed randomly throughout each agar bead 10 is a water-soluble, preferably polar, restraining polymer 14, preferably a quaternized cationic polymer, such as polyquaternium 24 or steardimonium hydroxyethylcellulose. Restraining polymer 14 is entrapped in agar gel 12 so that it is not readily leached or otherwise released therefrom so long as the bead 10 retains its integrity. Agar beads 10 can serve as a cosmetic delivery system for various active agents 16 which are bound to restraining polymer 14, for example ascorbic acid, lactic acid or papain, or alternatively they may be useful in their own right, without any further active ingredient, for example to deliver an entrapped restraining polymer, such as hyaluronic acid, a moisturizer, which has cosmetic or other active properties of its own. There are numerous possible alternative substances or materials to the preferred embodiments stated for agar gel 12, restraining polymer 14, and active agent 16, some of which are set forth hereinbelow. Others will be apparent to those skilled in the art.

As suggested schematically in FIG. 2, agar beads 10 can be manually crushed on the skin, preferably by an ordinary spreading or massaging action of one or more of the user's fingers 18, (or hands or equivalent other body parts, or implements), increasing the surface area of the agar beads 10 and bringing restraining polymer 14 into contact with the surface of the skin where normal skin constituents can release the active agent 10 from the restraining polymer 14, permitting it to permeate into the outer layers of stratum corneum skin cells 20. In FIG. 2, skin cells 20 have been exaggerated in size for clarity.

Continued spreading and massaging by the user's fingers 18 spreads the agar gel complex, with restraining polymer 14, over the skin surface where it can exercise its active properties, such as moisturizing, if it has any. Alternatively, if the polymer is substantially inert, along with the agar gel itself, the polymer will suffer one of the usual fates of cosmetic residues of being rubbed or washed off the skin or of being absorbed and enzymatically degraded or ultimately, if sufficiently inert, excreted.

Several different physico-chemical mechanisms of action are available to release active agents 16 from the restraining polymer 14 when the polymer 14 is exposed to the skin environment by crushing and spreading the agar beads. Sweat and sebum glands constantly discharge, respectively, moisture laden with various ionics, notably sodium chloride, at low strength, and a mix of lipids with phospholipids. The agar-polymer complex beads 10 of the invention are sufficiently large that they do not penetrate normal skin pores, follicular openings and the like. As the agar bead material is crushed and spread on the skin, its surface area increases providing an extended interface between the gel-polymer complex and any superficial skin moisture or lipids, initiating gradual release of active agent 16.

The ionic strength of skin moisture can break ionic bonds with the restraining polymer 14, encouraging migration of ionic active agents 16 to moist areas of the skin. Alternatively, the normal acidity of the skin, pH about 5.5, may release cationic actives 16 bound ionically to restraining polymer 14. In addition, natural skin lipids, such as sebum, may release lipophilically bound active agents.

If the skin is dry, with time, the gel-polymer complex can permeate through the skin moisture barrier constituted by the outermost keratinous layers of stratum corneum cells 20, and by the lipophilic "mortar" in the intercellular spaces 22, that bind cells 20 together, they encounter moisture and lipids to release actives. Such action may be encouraged by enzymatic lysing of the gel or polymer. The scope of the invention is not limited by the foregoing, or any other, theories or contemplated mechanism of action, which are provided by way of explanation, but only by the appended claims. What is significant is that the invention provides a delivery system which can successfully deliver actives to the skin surface and, if desired, protect those actives in cosmetic or other vehicles, during formulation or on the shelf, or both.

Some substances and materials usable in the practice of the invention are described in the following paragraphs. Others will be apparent to those skilled in the art.

Gel-forming agents: A particularly preferred gel-forming agent for use in the practice of the invention is agar, also known as "agar-agar". More properly referenced "agarose," which is the neutral gelling fraction of agar (the other being a sulfated non-gelling fraction "agaropectin"), the term "agar" is nevertheless used herein in the same sense as "agarose". Agar is an example of a gel-forming polysaccharide commonly used as a medium for electrophoresis and chromatography. Agar is insoluble when dispersed as a dry solid in water at low temperatures, however, it becomes soluble when heated to temperatures over 70-90° C. and forms a gel upon cooling. Agar is relatively expensive in comparison with some other commonly used gelling agents, but is particularly well suited for formulation with cosmetic vehicles, especially two-phase creams, gels and lotions which are usually homogenized at an elevated temperature. Agar gels are stable to both pH and moderate elevation of temperature.

Surprisingly, preferred embodiments of agar-polymer complex gel beads can be formulated into cosmetic creams, employing aqueous phase ingredients and temperatures as high as 80° C., without losing their integrity, and while continuing to protect contained actives. Agar gel beads are stable, once formed, and are difficult to solubilize in aqueous media, even at elevated temperatures. The beads of the invention are thus sufficiently durable to remain stable for the relatively short period at elevated temperature, e.g. up to about 10 minutes, required for homogenization of cream or other emulsions, and in fact should be stable for up to about 30 or 40 minutes. In addition, ungelled agar solutions are stable at temperatures as high as 100° C. which is advantageous for solids loading, permitting high concentrations of active and restraining polymer to be dissolved.

However, in preparing the agar-gel beads or formulating them into cosmetics, care should be taken to avoid exposing heat-sensitive agents to excessive heat, by adding them at lower temperatures, adding beads to cosmetic formulations after emulsification or by exposing beads containing such heat-sensitive actives for only short periods of time insufficient to be damaging.

While agar is a particularly preferred gel for use in the practice of the invention, other gels meeting the requirements of the invention can be used. Such other gels should be capable of forming dimensionally stable, self-supporting gel-polymer complex particles that are stable under the conditions of formulation, if any, (the particles themselves may constitute the end product), packaging and storage, and which can be crushed, spread or otherwise dispersed on the skin or nails of an end user to increase the surface area of the particles and disperse contained active in situ. The beads are preferably not unduly tacky and do not adhere to one another on contact. Preferred gels are water-soluble polymers that are pH stable. Preferably also, they should be such as can yield polymer-complex beads that are stable, when exposed with mixing, to an aqueous environment at about 50° C. for at least 5 and preferably 15 minutes. Still more preferably, the polymer complex beads produced should be stable, when exposed with mixing, to an aqueous environment at about 80° C., for at least 5, and preferably 15, minutes.

Other such possible gels will be known or apparent to those skilled in the art, in the light of the disclosure herein, and may include: synthetic polymers, such as vinyl or acrylamide polymers, or copolymers; natural polymers, for example polysaccharides, or proteins or synthetically modified ones of such polymers; botanically derived gels; and may include gelling agents such as carbopol, a common, low-cost petroleum-derived, cosmetic gel. However carbopol's gelling characteristics depend on pH levels, so that it not a suitable protectant for many actives for example alpha hydroxy acids.

It will be understood that the gel-forming agent selected for use in the practice of the invention should not only satisfy the particle or bead forming requirements described herein, but should also meet any requirements associated with the intended cosmetic, pharmaceutical, medicament, or other end use of the bead. Some other such gel-forming polymers are disclosed in Cini et al., supra, see for example, column 4, line 11 to column 6, line 30, the disclosure of which is hereby incorporated herein by reference thereto.

Restraining polymer. As stated above, the restraining polymer employed in practicing the invention has sufficient molecular weight to prevent egress of the restraining polymer from the agar gel, and has retention groups to bind the active agent to the restraining polymer for retention in the gel particles. Preferably also, it is water-soluble to a sufficient extent that a desired proportion can be co-dissolved with agar in an initial particle-forming step. The restraining polymer used is preferably selected according to the desired active agent or agents to have one or more retention groups which will bind the active agent.

Pursuant to the invention, it has been discovered that polymers with an average molecular weight of about 100,000 daltons, and more, are unable to flow through a preferred agar gel matrix. However, certain polymers, especially polymers capable of interacting with the agar, may be adequately retained in an agar gel, for the purposes of the invention even although they have a lower average molecular weight, e.g down to 75,000 daltons, or even as low as 50,000 daltons. There is no particular upper limit to the molecular weight of the restraining polymer, although it is contemplated that the average molecular weight will not exceed several million, e.g. 5 million daltons, but preferably does not exceed 1 million daltons. A preferred range for the average molecular weight is from 75,000 to 125,000 daltons.

Some preferred classes of restraining polymer are cationic polysaccharides and polypeptides or proteins. For example, some specific restraining polymers preferred for the practice of the invention are certain commercially available quaternized polysaccharides, especially celluloses, rich in quaternary groups, notably polyquaternium 24 available under the trademark QUATRISOFT LM-200 (Union Carbide Corporation), polyquaternium 11, available for example under the trade name GAFQUAT 755N (ISP Europe), and the CRODACEL Q (trademark) range of alkyl quaternary cellulose polymers (Croda, Inc.), notably laurdimonium hydroxyethylcellulose, sold under the trademark CRODACEL QL, cocodimonium hydroxyethylcellulose, sold under the trademark CRODACEL QM and steardimonium hydroxyethylcellulose, sold under the trademark CRODACEL QS. The CRODACEL Q (trademark) polymers belong to a class of polymers having repeating units of the following general nature:

[(anhydroglucose)(OC$_2$H$_4$OH)$_2$.(OC$_2$H$_4$)$_x$.C$_2$H$_4$OH.R$_1$N$^+$R$_2$.R$_3$.R$_4$CL$^-$]

where x is often unspecified but may be taken to be under 10 and may be 0; $R_1$ is commonly methylene; $R_2$ and $R_3$ are frequently methyl and $R_4$ is the characteristic longer alkyl group, e.g. 10-30 carbon atoms such as lauryl, cocoyl or stearyl. The polyquaternium 24 polymers lack the two hydroxyethyl substituents. Each anhydroglucose unit can have a maximum of three ethoxy substituents, as shown, but in practice, the average degree of ethoxy substitution will be substantially lower so that the indication of di-hydroxyethyl substitution should be regarded as a theoretical limit rather than a practical representation. Thus, each repeating anhydroglucose or saccharide unit contains up to two hydroxyethyl substituents and a quaternary ammonium group attached to the polysaccharide nucleus via a short polyethoxy chain. Polyquaternium polymers lack the longer alkyl group and the lipophilic character it confers.

Of particular importance is the quaternary nitrogen atom which provides a cationic binding site for anionic actives. The $R_4$ alkyl chain can provide a lipophilic anchor for lipid or lipophilic actives. the CRODACEL Q (trademark) range of quaternized celluloses are more fully described in a product data sheet entitled "Crodacel Q range" from Croda Chemicals Ltd., UK, the disclosure of which is hereby incorporated herein by reference thereto. They are supplied as somewhat hazy or opaque viscous concentrates intended for dilution and are known as film-forming agents with particular application in hair shampoos and conditioners, where their ability to be substantive to the hair, i.e. to attach themselves to the hair in a substantive manner, without creating build-up, is valuable.

These and similar polymers suitable for use in the practice of this invention are well known in the literature and are described, for example, in U.S. Pat. Nos. 5,135,748 (Ziegler et al.), 4,970,067 (Panandiker et al.), 5,288,484 (Tashjian) the disclosures of which are also hereby incorporated herein by reference thereto.

Quantitatively, it is theoretically possible for each polar group to bind one acidic molecule of the entrapped active, assuming the active molecule is small enough to fit. In order to produce an end-user cosmetic suspension with a desirably high concentration of active, the ionic bonding capacity should be as high as practical and so must be the number of cationic groups bonded to the polymer backbone. While ratios as low as 0.2 or close to the theoretical limit of 2.0 may be useful, an average ratio of 0.5 moles to 1.5 moles of quaternary groups per glucose unit is preferred to provide a high loading capacity of the active to the agar bead without too high of a proportion of polymer to agar. In practice, a commercially available ratio of 1.2 moles of quaternary groups per glucose unit was used, this being the approximate number for steardimonium hydroxyethylcellulose, a strong anion exchanger, can be used, as well as, weak anion exchangers (tertiary amines) and cation exchangers, either strong (sulfonate or phosphate groups) or weak (carboxyl groups).

Other polysaccharide polymers which, when suitably modified, can be used include starch, cellulose, chitosan and karageenan. Other polymers can be used such as modified proteins, polypeptides of adequate molecular weight, or non-biological polymers (e.g. acrylates). Protein-based or biological polymers may bring allergenicity problems, depending upon their heterogenicity, and are accordingly not preferred for use in the practice of the invention. However, relatively homogenous polyamino acids, e.g. polylysine, have low immunogenicity and are more suitable for use as the restraining polymer of the invention. The amino acid monomer, e.g one or more of the amino acid elements of natural polypeptides, can be selected to provide a desired retention unit, having desired binding characteristics with a particular target active, as will be apparent to those skilled in the art. Thus, at suitable pH levels, the basic, distal amino groups of polylysine or polyarginine can provide cationic retention moieties for anionic actives, while the distal carboxyl moieties of polyaspartic acid or polyglutamic acid, can provide anionic retention moieties for cationic actives.

The retention groups do not necessarily have to be covalently bound to the restraining polymer backbone, but may be provided as components of molecules complexed, or otherwise bound, or associated with the restraining polymer in a manner facilitating the retention of one or more desired active agents within the gel beads. The term "restraining polymer" as used herein includes such polymer complexes or associations. Accordingly, in manufacturing the beads, separate ingredients may furnish the polymer backbone and the retention groups. For example, the polymer backbone may be provided by a water-soluble or hydrolyzed protein, e.g. hydrolyzed whole wheat protein, such as available under the trade name HYDROTRITICUM 2000 (Croda Chemicals Ltd., UK), and cationic groups may be furnished by a quaternary amine salt having a substantial lipid character, e.g. behentrimonium methosulfate combined with cetearyl alcohol, available under the trade name INCROQUAT BEHENYL TMS (Croda Chemicals Ltd., UK), a self-emulsifying waxy substance. These latter two materials may be employed in relative anhydrous weight proportions of from about 1:10 to about 5:1, preferably about 5:1 to about 1:1 of hydrolyzed whole wheat protein to the commercially available INCRO- QUAT BEHENYL TMS product, to provide the restraining component of the invention. Other, equivalent products can be used to provide a comparable distribution of cationic (or possibly anionic, depending upon the active agent) groups in the resultant restraining polymer.

Other suitable restraining polymers which can meet the requirements of the invention will be known or apparent to those skilled in the art, based upon the teachings of the disclosure herein. Mixtures of different restraining polymers can also be used.

Actives: Some examples of classes of dermally active, or dermally effective substances having biological or cosmetic activity, which can be topically delivered employing the delivery systems of the invention include: antioxidants including botanically derived polyphenols, for example procyanidin oligomers; free radical scavengers; topically active enzymes, for example, antibacterials, such as glucose oxidase, antioxidants such as superoxide dismutase, and proteolytic enzymes such as bromelain and papain, (useful for enzyme peeling); other enzymes such as the DNA repair enzymes described above; exfoliative retinoids, such as retinol and retinol esters including retinol acetate, vitamin A palmitate; purified plant extracts and plant proteins; vegetable oils, for example, grape seed, sunflower, safflower and jojoba oil; essential fatty acids, such as linoleic acid, linolenic acid and arachidonic acid; animal proteins, for example collagen, elastin and keratin; moisturizers, such as hyaluronic acid and other glycosaminoglycans; whitening agents such as arbutin; ultraviolet light filters; coated or uncoated organic and inorganic pigments such as titanium, zinc, and iron oxides and anti-actinic suspensions or dispersions of such inorganic oxides; melanin or a sepia ink extract; other colorants or dyes, and perfumes.

While pigments and perfumes may have a role in enhancing the esthetic appeal of the carrier gel beads in which they are incorporated, they may also perform cosmetic functions when the gel beads are applied to the skin or other endogenous surfaces, for example, the nails or hair and then crushed, commencing controlled release of the actives. The release can, to some extent, be user controllable. Thus, for example, a user may firmly spread a body cream containing perfume-loaded gel-complex beads according to the invention, until they detect enough perfume is released or a rouge, makeup, foundation or other pigmented cosmetic, until the color is to their liking. The carrier beads and the respective proportions of their components may be adjusted to provide continued release to sustain the color or perfume intensity. In addition, the user may, with small, hard-to-see beads, refresh the active by further crushing and spreading residual uncrushed gel beads, at a later time.

In general, any active can be used that binds satisfactorily to the restraining polymer and can be released by contact with the skin. Many novel formulations and enhancements of known cosmetics that can be obtained by supplementing them with labile actives carried within and protected by the polymer-gel complex beads of the invention, will be apparent to those skilled in the art. One such product comprises a mixture of actives providing a novel prophylactic and therapeutic treatment for solar exposure comprises an ultraviolet absorbent or screening agent, for example titanium dioxide, an antioxidant, for example vitamin E, and a DNA repair enzyme, incorporated into agar-polymer complex beads, according to the invention. If desired, a melanocyte stimulant could be included. Such beads could be used per se, or incorporated into traditional creams or lotions.

Preferred Actives Some examples of particularly preferred actives for delivery by the gel carrier particles of the invention are: ascorbic acid (vitamin C), alpha-tocopherol (vitamin E), tocopherol acetate (vitamin E acetate), purified papain extract, beta-carotene, green tea extract rich in polyphenols, purified extracts of procyanidolic oligomers from grape seed or pine bark, monoazoic dye e.g. D&C orange, xanthenic dye (disodium salt), cinnamic acid and octylmethoxycinnamate.

Surprisingly, all of these materials can be effectively bound to a modified starch restraining polymer containing quaternary ammonium groups, incorporated in the protective gel carrier particles of the invention, and then formulated into a cosmetic cream so that they retain their activity, or cosmetic properties, when applied topically. Furthermore, multiple such actives can be similarly bound to a suitable restraining polymer and incorporated in protective gel carrier particles, to deliver their desired properties to end users in topical formulations, for example, an antioxidant combination of vitamins C and E, colored with three colorants, and one or more colorants combined with papain, or other such preferred active.

One preferred class of actives is anionic, a particularly preferred restraining polymer to which the actives bind being a modified polysaccharides containing quaternary ammonium groups which are cationic and are able to form stable ionic bonds with many anionic actives.

Water. Water is also a significant ingredient of the carrier particles of the invention, being the medium through which colloidal agar particles are dispersed to provide a semi-solid or nearly solid gel. Other aqueous media, or possibly, polar alcohols or glycols, may substitute for water. In preparing the agar beads of the invention, agar and other ingredients are mixed with water and injected through a needle as a warm solution or dispersion, at a speed controlled to generate drops, then cooled to set the gel.

Proportions. The proportion of solids to water should be sufficient to dissolve or disperse the solids and to ensure they will remain in solution or dispersed until desired gel formation in the oil medium, after the droplets leave the injection needle.

Preferably the solids comprise from about 0.5 to about 40 percent by weight of the solution or dispersion and more preferably from about 1.5 to about 25 percent by weight. The relative proportion of restraining polymer 14 to agar 12 can be as low as 1:10, but to obtain a satisfactory loading of active agent 16 (which can, in certain instances, be the polymer itself, e.g. hyaluronic acid) a proportion of at least 1:1, up to about 10:1 restraining polymer 14 to agar 12, is desirable. Preferably, a proportion of from about 2:1 to about 6:1 is used.

The proportion of active agent 16, assuming such to be additional to the restraining polymer 14, will usually be made as high as practical, without affecting the integrity of the particle or causing unacceptable instabilities in storage. The maximum practical loading of active, a desirable objective, will vary substantially, depending upon the nature of active agent 16 and will usually be related to the quantity of restraining polymer 14. Depending upon the potency of the active, and other factors such as its physical form, the proportion of active agent to restraining polymer may range from about 0.01:1 to about 10:1, preferably from about 0.1:1 to about 5.0:1. Preferably also, the active agent comprises from about 0.01 to about 20 percent of the solution, or dispersion, at the injection needle, more preferably about 0.1 to about 10 percent.

The foregoing relative proportions are, as previously stated, based on weight, and are also based on the ingredients of the solution or dispersion at the injection needle. With proper manufacturing or production procedures, these proportions should largely be reflected in the end product agar complex gel beads themselves, but variations may occur.

Cosmetic formulations. Cosmetic formulations, diluents or cosmetic vehicles are compositions applied externally to the skin, hair or nails for purposes of cleansing, beautifying, conditioning or protecting the body surface. Cosmetic formulations include but are not limited to water-in-oil or oil-in-water emulsions in cream or lotion form; sunscreens, toners, astringents, facial make-ups, powders, and skin cleansing compositions. The recipes for such compositions are well known to those skilled in the art and can be found in many publications in the field. A brief summary of some such cosmetic "diluents" that can be used in the practice of the invention appears in Wolf et al. U.S. Pat. No. 5,449,519, for example at column 4, line 25 to column 6, line 56, the disclosure of which is hereby incorporated herein by reference thereto. The gel-complex particles of the invention are generally suitable for incorporation into such cosmetic compositions or "diluents" and the invention extends to the resultant gel-complex particle containing compositions which have beneficial properties arising from the presence of the gel-complex particles, for example new active ingredients, new concentrations of active ingredients, or simply better delivery of active ingredients with reduced loss of activity.

The gel beads of the invention can be used in such cosmetic compositions in any desired concentration or proportion that will provide an effective amount of active agent upon application, for example from 0.1 to 90 percent by weight of the total composition, preferably from 1 to 50 percent, and more preferably from 5 to 25 percent by weight of the total composition.

Figure 3:
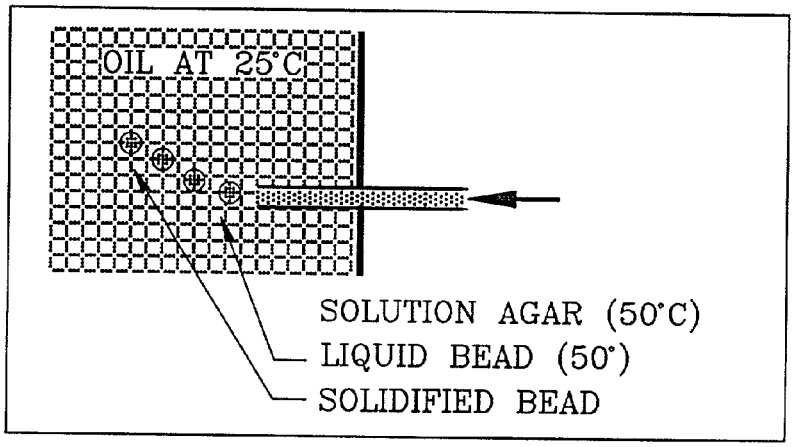
FIG. 3 is a schematic representation of a prior art process for making agar gel beads.

Manufacture. As shown in FIG. 3, it is known to make agar gel beads by dissolving granular agar in deionized or distilled water heated to an elevated temperature sufficient to dissolve the agar, using a proportion of agar to water effective to form a gel at lower temperatures, cooling the hot agar solution to a suitable intermediate temperature above the gelling point of the agar solution, typically about 30° C., and injecting the cooled solution through an injection needle, sized according to the desired agar bead size, into a hydrophobic liquid maintained at a temperature suitably below the agar gelling point for bead formation, at a rate of injection controlled to favor bead formation. As indicated in the illustrative example of FIG. 3, the dissolved agar is cooled to about 50° C. and injected into an oil medium, e.g. a paraffin bath, at about 2.5° C., whereupon the agar gel beads solidify as they leave the injection needle.

In the method of the invention, a suitable restraining polymer, and the active agent, if any, dissolved or dispersed in water or an aqueous solvent system, are mixed with the agar solution before injection into the hydrophobic liquid. Suitable restraining polymers, and many actives, are generally temperature stable and can be mixed with the agar granules and heated to the elevated temperature to provide a clear solution of all ingredients. Less stable actives, for example, enzymes, can be introduced to the agar-polymer solution at the intermediate temperature, preferably in aqueous solution or suspension.

The temperatures of both the agar mixture and the paraffin bath are chosen and adjusted according to the type of bead being produce, i.e. its constituents, toward the goal of providing separable, pourable beads which can be crushed or spread on the skin. In particular, they are adjusted to ensure that the viscosity of the hot agar mixture is low enough to permit the mixture to be pumped through the injection needle. The viscosity will vary with different bead formulations, being increased by higher concentrations of ionic actives.

Other methods of forming gelatinous beads will be known or apparent to those skilled in the art, and may be adapted to the purposes of the invention. For example, instead of injecting drops of warm agar solution into a cold oil bath, the warm solution may be dripped from above on to the surface of cold oily medium. A particularly efficient process comprises mechanically dispersing the warm solution in a cold immiscible oil or the like using an agitator. The rate, or degree of agitation determines the size of the gel beads produced.

If desired the active agent and the restraining polymer can be premixed to foster bonding of the active to the restraining polymer, in a preliminary step. Lipophilic acids, can if desired, be bonded to the restraining polymer in a preliminary mixing step employing a lipophilic solvent which is evaporated or otherwise removed prior to mixing with the agar solution.

The resultant beads comprise a complex of active-loaded restraining polymer entrapped in an agar matrix. The beads are soft, clear, glossy, odor-free and esthetically appealing, pH-stable and temperature stable to temperatures up to about 80° C. The hardness, or preferably softness of the beads is preferably carefully chosen, by appropriate selection of processing parameters, according to the bead components, so that the beads are hard enough to be conveniently handled, transferred from drums to formulation vessels, and the like, and hard enough to resist breakdown in mixers or homogenizers, yet soft enough to be crushed on the skin, and preferably sufficiently soft to be spread and "disappear".

A principal parameter affecting the hardness is the agar concentration (higher concentrations form harder beads), but oily actives will soften the beads and the concentration and composition of the restraining polymer can also affect the hardness of the bead. These parameters are preferably selected and controlled to provide the desired hardness, which is that of a soft, pleasant crushable feel.

Figure 4:
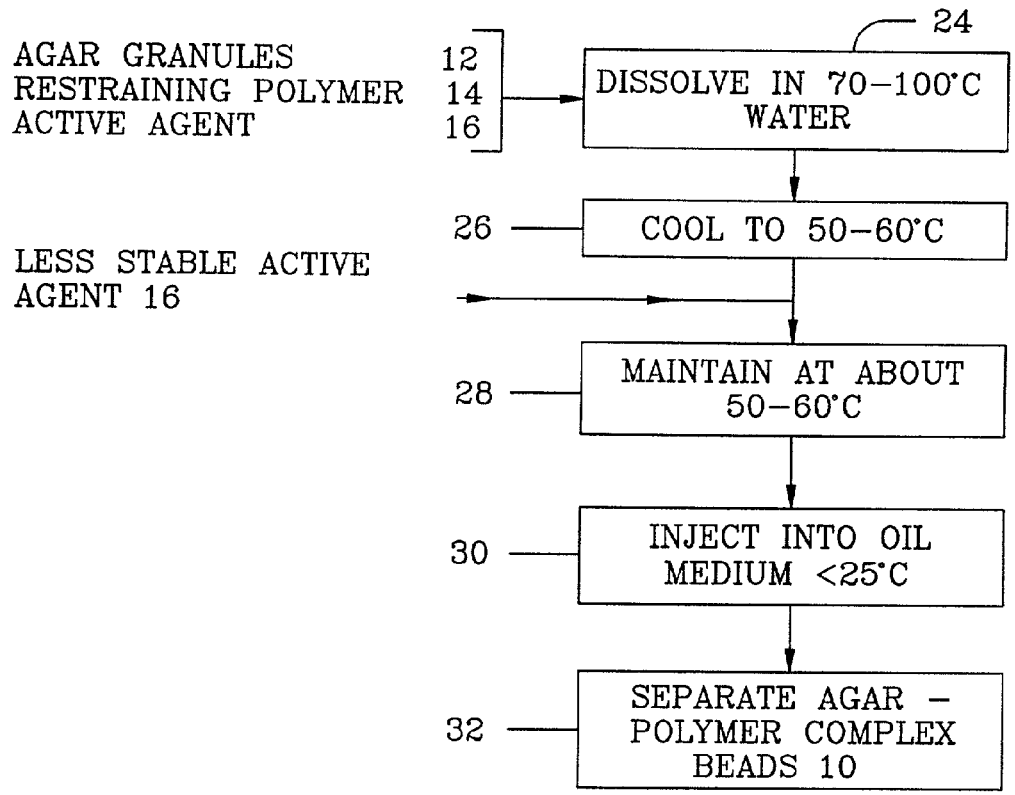
FIG. 4 is a block flow diagram of one method of manufacturing agar-polymer complex beads according to the invention.

Referring to the manufacturing process illustrated schematically in FIG. 4, agar granules 12, restraining polymer 14 and stable active agent 16, if used, are dissolved and, if appropriate, dispersed, in a mixing step 24 in deionized or distilled water, conducted at an elevated temperature, preferably between about 70 and about 100° C., more preferably between about 85 and about 95° C., or about 90° C. Upon heating, the suspension becomes a clear solution.

Optionally, the solution or dispersion is cooled in a cooling step 26 to an intermediate temperature above the gelling point of the solution or dispersion where less heat must be lost from the solution or dispersion to precipitate gelation. The intermediate temperature may range from about 40 to about 70° C., preferably from about 50 to about 60° C. Less stable actives, for example enzymes, dissolved or dispersed in water are incorporated in, and mixed with, the agar-polymer solution at the intermediate temperature to avoid detrimental effects of the higher temperature. Enzyme-containing solutions should be kept near to about 50° C. to avoid denaturing which may occur at temperatures around 60° C.

Preferably, the solution is temperature stabilized, at the intermediate temperature, for example, using a water jacket or bath, maintained at a temperature of about 50° C., in temperature-stabilization step 28.

The liquid solution or dispersion is then pumped through a needle submerged in a liquid paraffin oil bath maintained at a temperature below the gelling point of the solution or dispersion, namely below about 30° C., preferably below about 25° C., more preferably about 0 to 10° C., while mixing, in oil injection step 30. Because water and oil are immiscible, the pumped solution of warm agar, polymer and active, form droplets when extruded into the oil. The low temperature of the oil "freezes" the droplets in shape, causing the agar medium to gel into agar-polymer complex beads 10. Alternatively, the hot agar solution, from step 24, may be directly introduced to the cold oil at a rate such as to provide adequate cooling to provide bead formation.

The agar-polymer complex beads 10 are then separated, washed to remove the paraffin oil, filtered and dried, in separation step 32.

Figure 5:
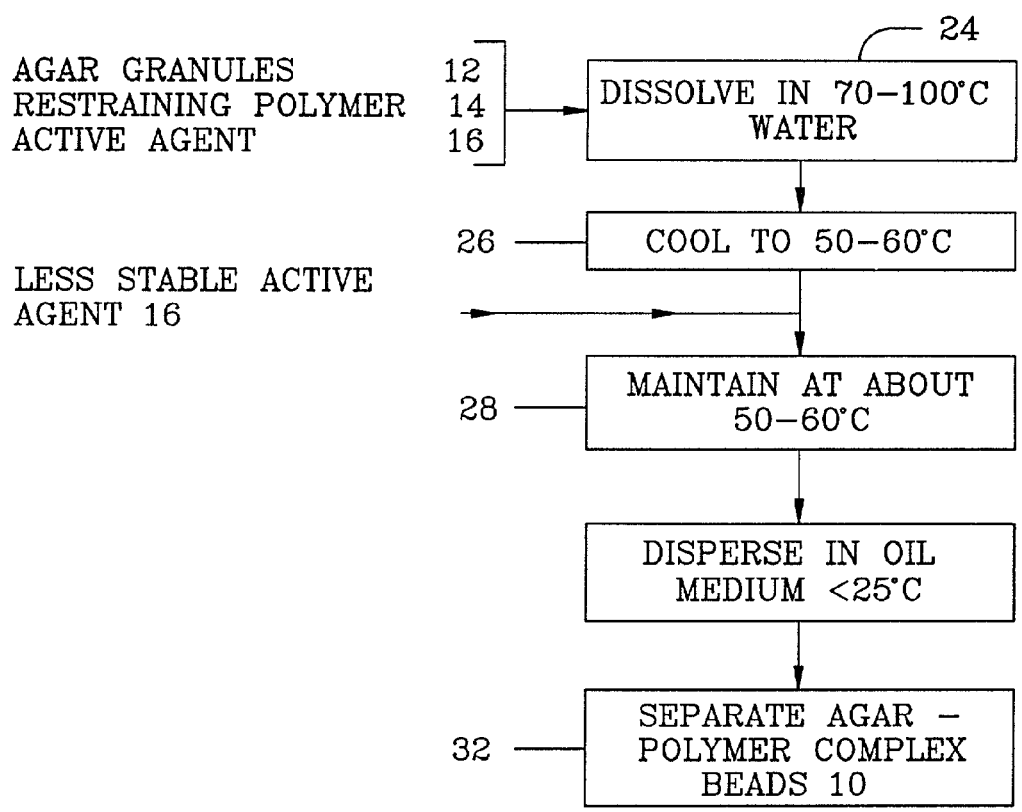
FIG. 5 is a block flow diagram of another method of manufacturing agar-polymer complex beads according to the invention.

Referring to FIG. 5, an alternative method of the invention does not require needle injection of the agar-restraining polymer solution into the cold oil bath. Preparation of the hot or warm agar-polymer solution in mixing step 24 and optional cooling step 26, with addition of active agent 16 at a suitable point, is similar to the process depicted in FIG. 4. The warm aqueous phase agar solution (or dispersion) is then introduced into a substantial excess of cold oil with agitation, for example by means of a rotating paddle. Rather than the relatively slow and more difficult process of feeding the solution through a submerged hollow needle, a relatively rapid, simple pouring step suffices to introduce the aqueous phase to the colder oil. The components of the two phases are selected to be immiscible so that beads will form as the dispersion is agitated. The average size of the beads can be controlled by the speed of agitation and it is preferably under 5 mm, more preferably from about 2 microns to about 1.5 mm.

Large gel particles or beads, up to approximately 2 mm in diameter, can be colored, filled with actives and formulated in a transparent gel, the colorants and actives being incorporated in the injection solution or dispersion. Different sized beads can be produced by adjusting the size of the needle diameter or the agitation speed of the oil bath, higher speeds producing smaller beads.

Some non-limiting examples of the practice of the invention will now be described by way of illustration.

Example 1

Preparation of Agar Complex Beads Using Polyquaternium 24

1.5 g of agar granules (OSI-France) with a gelling point of about 33° C. and 1.5 g of polyquaternium 24 [QUATRISOFT LM-200 trademark Union Carbide Corporation (Amerchol-France)] are mixed in 97 g of distilled water and heated to 90° C. The suspension becomes a clear solution at this temperature and it is then allowed to cool to 50° C. in a water bath. The solution is then pumped through a needle by means of a peristaltic pump (Bioblock-France) and the needle is placed into a liquid paraffin oil bath maintained at 5° C. while mixing (250 rpm). The pump flow rate is adjusted to 2.5 ml/minute and the liquid is injected into the oil bath. Gel beads are formed in the oil phase and their size depends upon the inner diameter of the needle. For this example, two different sized needles were used: 0.45×12 mm or 0.8×50 mm (inner diameter×length). The gel beads are separated by filtration on a 0.2 mm screen and extensively washed with water. In this example, 2 mm diameter beads are typically formed. Smaller beads are formed using higher mixing rates (e.g. 1200 rpm) while smaller needle diameters help maintain small diameter. The gel beads formed are smooth, shiny and soft. Surprisingly, the presence of the restraining polymer does not significantly alter the ability of the agar to gel and form stable beads when cooled in oil.

Example 2

Preparation of Agar Complex Beads Using Hyaluronic Acid as Anionic Copolymer

The procedure of Example 1 is followed except hyaluronic acid (Soliance-France) is mixed with the agar instead of polyquaternium 24. The beads formed by this procedure are suitable for use either as a moisturizer, delivering hyaluronic acid, or as a delivery system for cationic actives attached or bound to the hyaluronic acid.

Example 3

Preparation of Agar Complex Beads Using Steardimonium Hydroxyethylcellulose

The same procedure as in Example 1 is used, except that 7.5 g of steardimonium hydroxyethylcellulose (CRODACEL QS, trademark, Croda, Inc.) is substituted for the polyquaternium 24. Similar beads are obtained after extrusion into a 5° C. oil bath.

Example 4

Preparation of Agar Complex Beads Containing an Enzyme, Papain 1.5 g of agar and 7.5 g of steardimonium hydroxyethylcellulose are mixed in 56 g of distilled water and heated to 90° C. under mixing to obtain a clear solution. The mixture is allowed to cool at 60° C. and 5 g of papain in 30 g of distilled water is added to the solution. The mixture is maintained at 50° C. in a water bath, then injected into liquid paraffin oil at 5° C. under mixing (250 rpm). 2 mm diameter beads are formed, separated and washed with water.

Example 5

Preparation of Agar Complex Beads Containing a Colorant

Following the procedure of previous examples, 1.5 g of agar, 7.5 g of steardimonium hydroxyethylcellulose and 0.5 g of FD&C Blue (Colorants Wackherr-France) are dispersed together in 90.5 g of distilled water. The 2 mm diameter beads are formed in the oil bath, then separated and washed with water.

Example 6

Preparation of Agar Complex Beads Containing a Plant Extract

Following the procedure of previous examples, 0.6 g of agar, 0.2 g of steardimonium hydroxyethylcellulose (trademark), 1.0 g of polyquaternium 24 and 1.0 g of green tea extract (Rahn AG Switzerland) are dispersed in 30 g of distilled water and heated to 90° C. under mixing. 2 mm diameter beads are formed in the oil, then separated and washed with water.

Example 7

Preparation of Agar Complex Beads Containing a Lipophilic Active, Beta-Carotene 1.5 g of agar is dispersed in 70.5 g of water and heated to 90° C. under mixing to obtain a clear solution which is allowed to cool at 60° C. Then 7.5 g steardimonium hydroxyethylcellulose and 0.5 g of β-carotene (Cooperation Pharmaceutique Française-France) predispersed in oil, is dispersed in 20 g of distilled water and mixed with the above solution. The restraining polymer facilitates dispersion of the hydrophobic β-carotene. The mixture is maintained at 50° C. and injected through a needle (0.45×12 mm) into liquid paraffin oil at 5° C. under mixing. The beads produced containing the β-carotene have an average diameter of 2 mm.

Example 8

Preparation of Agar Complex Beads Containing Both Hydrophilic and Lipophilic Actives: Vitamin C and Vitamin E Following the procedure of Example 7, 1.5 g of agar, 7.5 g of steardimonium hydroxyethylcellulose, 7.5 g of ascorbic acid (Cooperation Pharmaceutique Française-France), 2.5 g of α-tocopherol (Fluka-Switzerland) are mixed in 81 g of distilled water. 2 mm diameter beads containing vitamins C and E are obtained in the oil phase, then separated and washed with water.

Example 9

Preparation of Agar Complex Beads Containing a Pigment

Following the procedure of Example 7, 1.5 g of agar, 1.5 g of steardimonium hydroxyethylcellulose, 5 g of titanium dioxide (ADF Chimie-France) and 2.5 g of iron oxide (Kobo Products USA) are mixed in 89.5 g of distilled water. 2 mm diameter beads containing the pigment are formed in the oil phase, then separated and washed with water.

Example 10

Modification of the Preparation Method for Agar Complex Beads

Following the procedure of the previous Examples, a clear agar solution with various additional ingredients, as recited, is maintained at 50° C., then pumped through a needle. However, in this example, the needle is placed 10 cm above the surface of the paraffin oil bath. Individual droplets are formed in air and fall into the cooled liquid, generating beads. The beads have the same appearance as the above described beads but their average size also depends upon the agitation speed of the oil bath. 0.5 mm to 2 mm diameter beads can be generated using the same type of needle with speed rates ranging from 100 rpm to 250 rpm. The gel beads formed are smooth, soft and shiny.

Example 11

Preparation of Agar Complex Beads by Dispersion with Agitation 1.5 g of agar-agar, 7.5 g of aqueous Crodacel-QS (containing 1.5 g of PG-hydroxyethylcellulose stearyldimonium chloride) are mixed with 91 g of water and are heated to a temperature above 80° C. for 15 minutes. The mixture is cooled to 50° C. and poured into a 1000 ml beaker containing 350 ml paraffin oil at 10° C., while mixing the oil phase with a motor and a U-shaped paddle at about 200 rpm. Approximately 1-millimeter beads of the aqueous phase are formed in the oil phase and, the low temperature of the oil induces gelling. After about 10 minutes, the oil phase is filtered on a 500 micron stainless steel sieve and the beads are thoroughly washed with water.

Example 12

Preparation of Vitamin-E-Loaded Agar Complex Beads by Dispersion with Agitation

In this example, the entrapped compound, vitamin E, is heat sensitive and would be damaged if heated to 80° C. Accordingly, the agar solution is cooled before adding vitamin E. 1.5 g agar-agar are mixed with 50 g of water and heated over 80° C. for 15 minutes. Separately, 7.5 g of aqueous Crodacel-QS (containing 1.5 g of PG-hydroxyethylcellulose stearyldimonium chloride) are mixed with 2 g of alpha-tocopherol (Roche, Switzerland) and with 39 g of water. The agar mixture is cooled to about 60° C. and the Crodacel QS mixture is added. The resultant mixture is further cooled to about 50° C. and poured into a 1000 ml-beaker containing 350 ml paraffin oil at 10° C., while mixing the oil phase with a motor and a U-shaped paddle at about 200 rpm. Approximately 1-millimeter beads of the aqueous phase are formed in the oil phase and, the low temperature of the oil induces gelling. After about 10 minutes, the oil phase is filtered on a 500 micron stainless steel sieve and the beads are thoroughly washed with water.

Example 13

Preparation of Agar Complex Beads Using Polyquaternium 11

The procedure of Example 11 is repeated except that 10 grams of a 20% aqueous solution of polyquaternium-11 (Gafquat 755N) is substituted for the Crodacel-QS solution.

Example 14

Preparation of Agar Complex Beads Using a Combination of Hydrolyzed Wheat Protein with Cetearyl Alcohol and Behentrimonium Chloride as a Cationic Restraining Polymer 1.5 g agar-agar are mixed with 50 g of water and the preparation is heated to at temperature in excess of 80° C. for 15 minutes. 1.5 g of Incroquat Behenyl TMC (behentrimonium methosulfate combined with cetearyl alcohol) are heated to 80° C. 6 g of water are separately heated to 90° C. and slowly added to the melted Incroquat Behenyl TMC and mixed for 15 minutes to obtain an emulsion. 0.5 g of hydrolyzed wheat protein are added to the emulsion. which is cooled to 50° C. When the agar-agar solution has cooled to 60° C., it is mixed with the protein-containing Incroquat Behenyl TMC emulsion. 40.5 g of water are added, the product is mixed and poured into an oil phase comprising 350 ml paraffin oil in a 1000 ml beaker, under mixing, 200 rpm). The beads are formed and sieved as described in Example 11.

The gel beads formed by the methods of Examples 11-14 are smooth, soft and shiny with an attractive appearance and little or no odor. They are stable at room temperature and can be readily crushed on the skin enabling the bead interiors to be spread topically, with a pleasant cool feel.

Activity Test

Activity of Ascorbic Acid after Entrapment within Agar Complex Beads

To determine if an active remains stable after its entrapment within mixed-agar beads, the activity of the ascorbic acid is measured by a DPPH test. In this test, 2,2 diphenyl-1-picrylhydrazyl (DPPH), a stable free-radical that exhibits an absorption band at 515 nm (violet color) which disappears upon reduction by an anti-free-radical agent.

Ascorbic acid is entrapped within the mixed-agar beads as set forth in the procedure in Example 8. Three 2 mm diameter beads containing an average ascorbic acid content of 2.25 mg and weighing approximately 30 mg each, were added to 3.5 ml of methanolic DPPH solution (DPPH concentration $0.6 \times 10^{-5}$ mol).

The beads were crushed in the test tube and the violet coloration attached to the DPPH disappeared within a few seconds. The experiment demonstrated that ascorbic acid entrapped in a complexed agar beads according to the invention retains its free radical scavenging activity.

Many materials can be added to the gel system, including fragrances and colorants, so long as they do not prevent satisfactory gel formation. However, care may be required with regard to liquids too much of which may impair the physical stability of the gel beads. Preferably, the proportion of liquid in the gel system additional to agar, restraining polymer and active agent is selected so that gelling is not prevented. While excesses of water may result in soft or poorly defined beads that are acceptable for some purposes, certain organic solvents may prevent bead formation. In particular, it is preferred to avoid excess proportions of organic solvents such as dipropylene glycol or butylene glycol that are often used in fragrances. The following comparative Example A demonstrates this point.

Comparative Example A

Non-Gelling Agar Complex Composition

Example 1 is repeated using 1.5 g of agar granules, 7.5 g of CRODACEL QS (trademark, Croda, Inc.), containing 1.5 g PG-hydroxyethylcellulose stearyldimonium chloride, 97 g. of water, or other quantity sufficient for bead formation in the absence of organic solvent, and 10 g dipropylene glycol. No significant beading occurs.

Comparative Example B

Other Non-Gelling Agar Complex Compositions

Comparative Example is repeated using solvated fragrance or butylene glycol in place of the dipropylene glycol. Again, no significant beading occurs.

Comparative Example C

Further Non-Gelling Agar Complex Compositions

Comparative Example A is repeated using pigments or active ingredients, as described herein. Again, no significant beading occurs.

Since such solvents can perform useful functions in a gel bead system, for example as vehicles for fragrances, it would be desirable to solve the problem of forming a satisfactory gel in the presence of such solvents. Pursuant to the present invention, this problem can be solved by providing the solvent or other material in its own carrier system to protect the gel medium from the effect of the solvent.

To this end, it has been discovered pursuant to this aspect of the invention that such gel-inhibiting solvents can be effectively trapped in porous inert particles, for example silica spheres, or porous microspherical inert polymers, such as polyethylene or polypropylene which particles provide an effective carrier system for the solvent and surprisingly, do not themselves interfere with gel formation. Such particles are preferably at least one or two orders of magnitude smaller than the gel beads in which they are incorporated, being for example from about 0.5 to about 100 microns in diameter, preferably from about 1 to about 30 microns and more preferably from about 3 to about 12 microns in diameter. Suitable adsorbent silica particle products are supplied by Kobo Products, Inc., South Plainfield, N.J., USA.

Pursuant to this aspect, the invention provides a method of making gel beads, or other gelled product, especially a gelled product intended for incorporation into a cosmetics product, the method comprising adsorbing a gel-inhibiting solvent on porous silica particles, or the like and dispersing the solvent-laden particles in a gelling medium, the gelling medium comprising a solution or dispersion of a suitable gelling agent, for example, an aqueous solution of agar, the preferred gelling agent described herein. The gelling medium is then formed into the desired gelled product as described herein, or as otherwise apparent to those skilled in the art.

It will be understood by those skilled in the art that this aspect of the invention has general application to enable a wide variety of solvents or other liquids to be incorporated into a gelling system by loading the solvent into protective carrier particles.

Example 15

Formation of Agar Beads with Solvent 10 g dipropylene glycol or a comparable fragrance solvent are mixed in a beaker or other vessel, with 1.6 g oil-absorbent silica shells (Kobo Products, NJ, apparent density 0.5-1.0 grams per cubic inch, oil absorbency from 550-700 g/110 g) to obtain a thick slurry or paste-like product. The thick product is dispersed in 7.5 g of CRODACEL QS (trademark, Croda, Inc.), containing 1.5 g PG-hydroxyethylcellulose stearyldimonium chloride, as described above in connection with the addition of active agents. A hot aqueous agar solution, containing 1.5 g of agar granules dissolved in 97 g. of water, or other quantity sufficient for bead formation in the absence of organic solvent, is added and the mixture is injected or dispersed in cold oil to yield well-formed, stable beads, with a good and consistent texture and size.

Example 16

Agar Complex Beads Employing Quaternized Silk Hydrolysate

Example 1 is repeated employing, as a restraining polymer, an equivalent amount of quaternized silk hydrolysate, PROMOIS (trademark) S-CAQ (Seiwa Kasei Co., Ltd.). Comparable results are obtained.

According to another embodiment of gel bead manufacturing method according to the invention it has been found that gel beads can advantageously be formed by entraining a liquid source of hot gel solution in a controlled flow of a cool oil stream, preferably moving with an approximately constant velocity.

Figure 6:
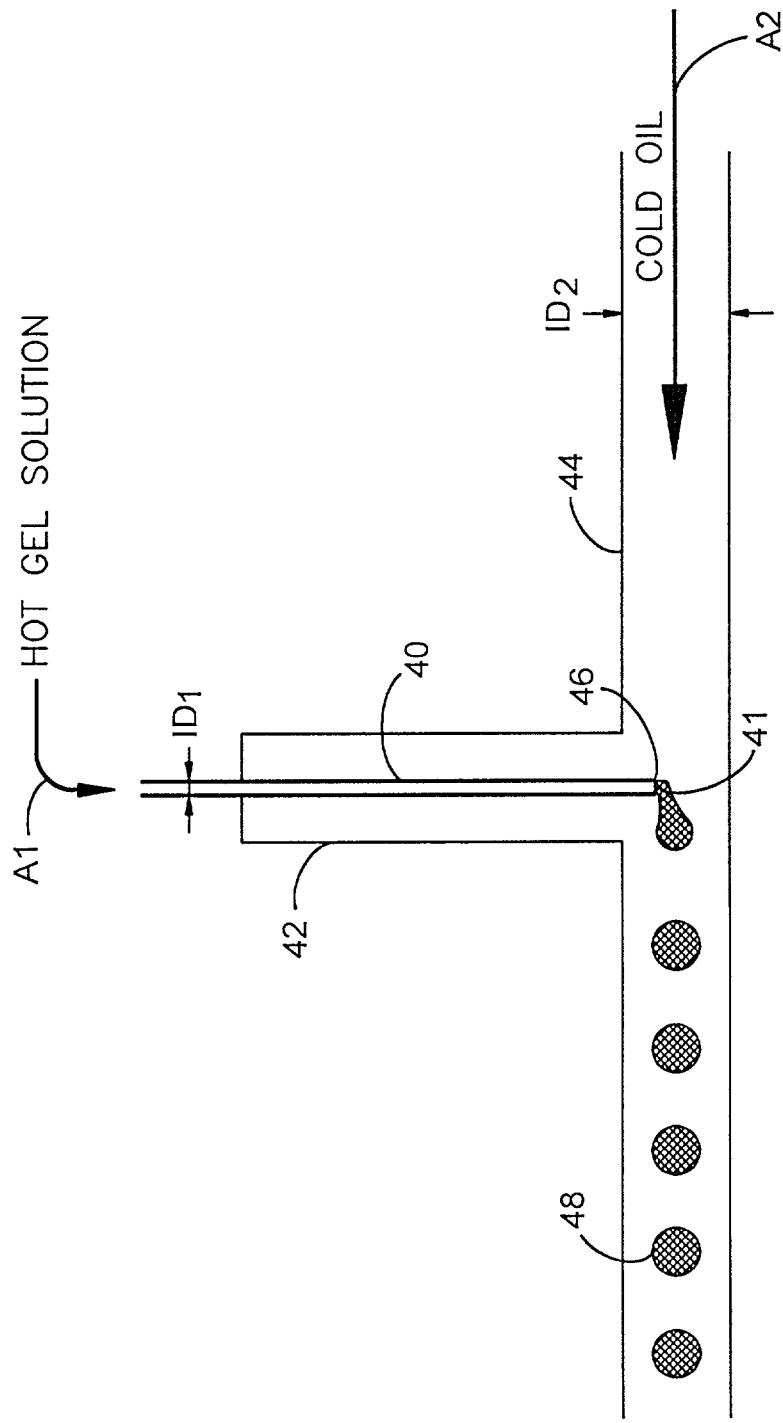
FIG. 6 is a schematic view of another method of making gel beads according to the invention.

Referring to FIG. 6, In a preferred embodiment of the method, the hot gel solution is supplied in the direction of arrow A1 to a venturi tube 40 having an internal diameter $ID_1$. Venturi tube 40 is supported in a side branch 42 of a conduit 44 having an internal diameter $ID_2$ through which cold oil flows in the direction of arrow A2, drawing gel solution from venturi tube A1. Side branch 42 is shown as extending perpendicularly to conduit 44. This apparatus can provide consistent high quality bead formation with a sharp cutoff of the forming bead from venturi tube 40. However, other angles could be employed. For example, venturi 40 could be at an acute angle of up to 45°, delivering the gel solution in the direction of flow of the cold oil. Alternatively, the tip 46 could be turned in the oil flow direction. However, such configuration may impede efficient breaking off of beads 48 from the stream of gel solution.

The bead size is related to the internal diameter $ID_1$ of venturi tube 40 and also to the oil flow rate, higher oil flow rates generating smaller beads and vice versa. Since rapid cooling of the gel solution is desirable to promote quality bead formation, both the flow rate of the oil and the diameter $ID_2$ of conduit 44 are preferably greater than the flow rate of the gel solution and the diameter $ID_1$ of venturi tube 40. Preferably, diameter $ID_2$ is at least twice that of $ID_1$, more preferably at least five times and possibly as much as ten times as large. Thus, the cross-sectional area of conduit 44 can be from 4 to 100 times, preferably 4, and more preferably 25 times the cross-sectional area of venturi tube 40. Preferred oil flow rates are also much higher than gel solution rates, for example at least twice as high, more preferably four to twenty times as high. For small beads oil flow rates may be 50 times higher. In general, the flow rate of the gel solution will depend upon its viscosity.

Some exemplary quantities employ a venturi tube 40 with an $ID_1$ of about 0.8 mm and an oil flow conduit 44 with and $ID_2$ of about 8 mm. Employing an agar solution, as described herein, the agar solution flow rate can be from about 2.5 to 6.2 ml/min. Oil flow rates can vary between about 10 and about 300 ml/min. with lower rates being useful for making larger beads of about 2.8 to about 4 mm diameter, and the higher flow rates being useful for making smaller beads of about 0.4 to about 0.7 mm diameter.

Figure 7:
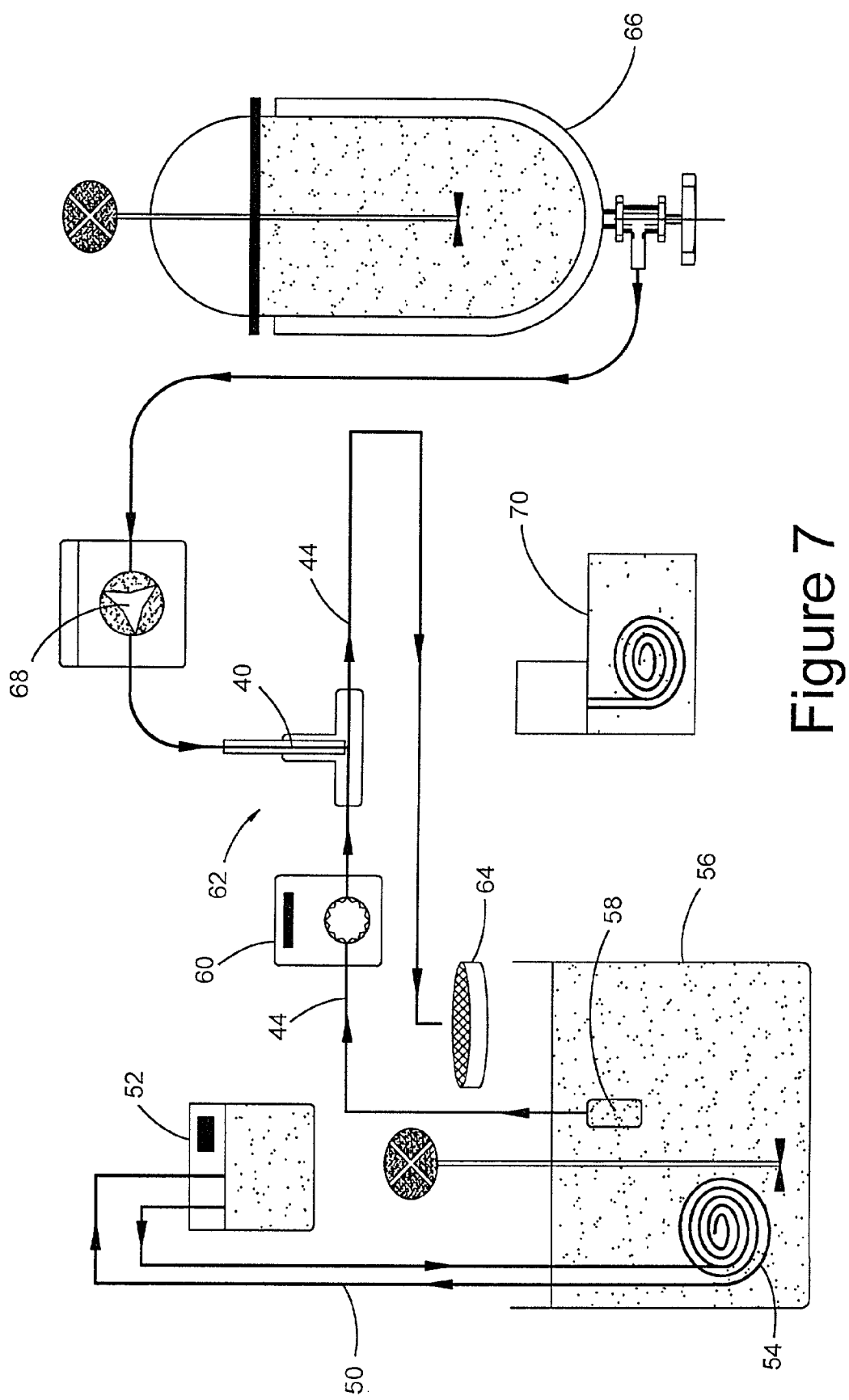
FIG. 7 is a schematic view of apparatus for manufacturing gel beads by the method illustrated in FIG. 6.

FIG. 7 illustrates an apparatus suitable for large scale manufacture of gel beads, employing the method illustrated in FIG. 6. Referring to FIG. 7, coolant fluid 50 recirculates from a chiller 52 to an immersion probe 54 immersed in an oil tank 56. Oil is drawn through a filter 58 by a gear pump 60 and delivered to conduit 44 mounted in a tee 62. Gel beads are removed from the emergent stream by a screen 64. Gel solution is mixed in a jacketed glass vessel 66 and delivered to venturi tube 40 by a peristaltic pump 68. If desired, the gel beads can be removed from screen 64 to water bath 70.

The methods and apparatus described herein are generally suitable for making any of the inventive bead compositions described.

While reference has been made to topical application of compositions containing the novel gel particle delivery systems of the invention, it will be understood that certain such gel delivery systems can, with benefit, be applied to tissues, e.g. wound tissue, and to other environments where the controllable release protection of actives, especially actives dispersed in an excipient, is important and where release of bound actives can be readily initiated.

INDUSTRIAL APPLICABILITY

The present invention is particularly suitable for application in the cosmetic industry providing novel consumer cosmetic products, for example, creams, gels and lotions containing gel-complex beads and the gel-complex beads themselves.

In addition, the ability of the agar complex beads of the invention to deliver labile, biologically active agents to the epidermis makes it possible to contemplate novel anti-actinic cosmetic compositions providing three lines of defense against the ravages of ultra-violet or other solar radiation. The first line of defense is a filtering agent, for example a zinc oxide or titanium dioxide dispersion to screen out ultraviolet or other undesired radiation. The second line of defense is a free-radical scavenger, for example vitamin E, or vitamin C, to repair or prevent damage at the molecular level and the third line of defense is a DNA repair enzyme, as referenced hereinabove to repair damage at the genetic level. These three defensive agents can, according to another aspect of the invention, be provided in a single anti-actinic composition, formulated with excipients as known to those skilled in the art, in amounts known to be effective for the individual defensive agents. The agar-complex gel beads described hereinabove provide a particularly preferred delivery vehicle for the DNA repair enzyme, possibly also for the free-radical scavenger and optionally for the screening agent. While all three agents might be delivered in the same beads, an alternative option is to use different beads for different agents, or combinations of agents, provided that they are substantially uniformly distributed in the end product so that the end-user can generate a suitable mixture of active agents by crushing and spreading a multiplicity of beads on the skin. Equivalents of the individual defensive agents that may be used in such a three-line anti-actinic composition, and other means of delivering them in a cosmetic or therapeutic composition, besides the gel beads described herein, will be apparent to those skilled in the art.

While some illustrative embodiments of the invention have been described above, it is, of course, understood that various modifications and equivalents of the described embodiments will be apparent to those of ordinary skill in the art. Some equivalents will be readily recognized by those of ordinary skill while others may require no more than routine experimentation. Such modifications and equivalents are within the spirit and scope of the invention, which is limited and defined only by the appended claims.

The invention claimed is:

1. A method of preparing a gel delivery system comprising gel particles for topical application of at least one active agent, said method comprising:
   (a) forming an aqueous solution of a polymeric gelling agent, said aqueous solution being maintained at a first temperature above the gelling point of said polymeric gelling agent, the solution being gellable at a lower temperature below the solution temperature, said aqueous solution forming a gelling agent solution further comprising, dispersed therein, said at least one active and a restraining polymer;
   (b) discharging the gelling agent solution through a discharge orifice into a moving stream of hydrophobic liquid and forming droplets of said gelling agent solution, said hydrophobic liquid being at a second temperature below the gelling point of said gelling agent solution, the hydrophobic liquid being immiscible with the gelling agent solution;
   wherein the gel particles coalesce from the gelling agent solution in the hydrophobic liquid stream through the gelling of said droplets with said active and said restraining polymer entrapped therein, and wherein the restraining polymer has sufficient molecular weight to prevent egress of the restraining polymer from the gel particles, and wherein said restraining polymer is bonded to the at least one active agent in the gelling agent solution so as to retain the at least one active agent in the gel particles;

wherein the restraining polymer includes at least one quaternary ammonium group or includes a complex comprising a water-soluble or hydrolyzed protein and a quaternary amine salt;

wherein the active is a dermally active or dermally effective substance having biological or cosmetic activity.

2. A method according to claim 1 wherein the hydrophobic liquid stream is contained in a conduit, the discharge orifice is located in the conduit and wherein the hydrophobic liquid stream moves past the discharge orifice and exerts a force on said solution in the discharge orifice, the force acting to withdraw said solution from the discharge orifice.

3. A method according to claim 1 comprising discharging the gelling agent through an injection tube, the injection tube terminating in the discharge orifice wherein the discharge orifice is positioned in the moving stream of hydrophobic liquid.

4. A method according to claim 3 comprising containing the hydrophobic liquid stream in a conduit wherein the liquid stream flows through the conduit and wherein the injection tube extends into the conduit.

5. A method according to claim 4 wherein the conduit has a rectilinear portion and the injection tube extends approximately perpendicularly into the rectilinear portion of the conduit.

6. A method according to claim 4 wherein the conduit has a cross-sectional area of from about 4 to about 100 times the cross-sectional area of the injection tube.

7. A method according to claim 4 wherein the ratio of the flow rate of the gelling agent solution to the flow rate of the hydrophobic liquid is between about 1:2 and 1:50.

8. A method according to claim 4 wherein the injection tube has an internal diameter of from about 0.05 to about 10 mm.

9. A method according to claim 4 wherein the conduit has a cross-sectional area of from about 4 to about 400 times the cross-sectional area of the injection tube, the ratio of the flow rate of the gelling agent solution to the flow rate of the hydrophobic liquid is between about 1:2 and 1:50 and the injection tube has an internal diameter of from about 0.05 to about 10 mm.

10. A method according to claim 4 comprising cooling the hydrophobic liquid upstream of the discharge orifice.

11. A method according to claim 10 comprising separating the gel particles from the hydrophobic liquid and recirculating the hydrophobic liquid to the discharge orifice.

12. A method according to claim 1 wherein the hydrophobic liquid stream is contained in a conduit, the gelling agent is discharged through an injection tube and the injection tube terminates in the discharge orifice, the discharge orifice being located in the conduit and wherein the hydrophobic liquid stream moves past the discharge orifice and exerts a force on the solution in the discharge orifice, the force acting to withdraw the solution from the discharge orifice.

13. A method according to claim 12 wherein the gel particles are capable of being manually crushed and applied topically by an end user.

14. A method according to claim 12 wherein the gelling agent comprises a pH stable water-soluble polymer selected from the group consisting of vinyl polymer and copolymers, acrylamide polymers and copolymers, polysaccharides, proteins, synthetically modified polysaccharide, synthetically modified proteins, botanically derived gels and carbopol.

15. A method according to claim 1 comprising pumping the gelling agent solution from a heated vessel containing a bulk supply of the gelling agent solution to the discharge orifice.

16. A method according to claim 15 comprising recirculating the hydrophobic liquid through a cooled tank.

17. A method according to claim 16 comprising recirculating a coolant between a chiller and the cooled tank to maintain a desired low temperature in the tank.

18. A method according to claim 15 comprising flowing the hydrophobic liquid containing gel particles over a screen to separate the gel particles from the hydrophobic liquid.

19. A method according to claim 1 comprising pumping the gelling solution from a heated vessel containing a bulk supply of the gelling agent solution to the discharge orifice, recirculating the hydrophobic liquid through a cooled tank, recirculating a coolant between a chiller and the cooled tank to maintain a desired low temperature in the tank and flowing the hydrophobic liquid containing gel particles over a screen to separate the gel particles from the hydrophobic liquid.

20. A method according to claim 1 wherein the discharge orifice includes an inner diameter and the moving stream of hydrophobic liquid has a velocity; the method further comprising selecting the inner diameter of the discharge orifice and the velocity of the moving stream of hydrophobic liquid according to the desired gel particle size.

21. A method according to claim 1 wherein the flow rate of the hydrophobic liquid is greater than the flow rate of the gelling agent solution.

22. A method according to claim 1 comprising discharging the gelling agent solution into the cold hydrophobic liquid stream at a flow rate of from about 2.5 to 6.2 ml/min wherein the hydrophobic liquid stream moves with a flow rate of about 10 ml/min to about 300 ml/min.

23. A method according to claim 1 operated to make beads of from about 2.8 to about 4 mm diameter or from about 0.4 to about 0.7 mm diameter.

24. Gel beads produced by a method according to claim 1.

25. The method of claim 1, wherein the restraining polymer is ionically bonded to the at least one active agent.

26. The method of claim 25, wherein said first temperature ranges from between about 70° C. and about 100° C.

27. The method of claim 25, wherein said second temperature is about 30° C. or below.

28. A method of preparing a gel delivery system comprising gel particles for topical application of at least one active agent, said method comprising:
  a) forming an aqueous solution of a polymeric gelling agent, the solution being gellable at a temperature below the solution temperature, said aqueous solution having a temperature ranging from between about 70° C. and about 100° C.; said solution forming a gelling agent solution further comprising, dispersed therein, said at least one active agent and a restraining polymer;
  b) discharging the gelling agent solution through a discharge orifice into a moving stream of hydrophobic liquid and forming droplets of said gelling agent solution, the hydrophobic liquid being immiscible with the gelling agent solution and being at a temperature of about 30° C. or below, said temperature below the gelling agent solution gelling point;
  wherein the gel particles coalesce from the gelling agent solution in the hydrophobic liquid stream through the gelling of said droplets with said active and said restraining polymer entrapped therein, and wherein the restraining polymer has sufficient molecular weight to prevent egress of the restraining polymer from the gel particles, said restraining polymer being ionically bonded to the at least one active agent in the gelling agent solution so as to retain the at least one active agent in the gel particles;

wherein the restraining polymer includes at least one quaternary ammonium group or includes a complex comprising a water-soluble or hydrolyzed protein and a quaternary amine salt;

wherein the active is a dermally active or dermally effective substance having biological or cosmetic activity.

29. A gel delivery system, comprising gel particles for topical application of at least one active agent produced according to the method of claim 1.

* * * * *